US005849720A

United States Patent [19]

Jamas et al.

[11] Patent Number: 5,849,720
[45] Date of Patent: Dec. 15, 1998

[54] ENHANCEMENT OF NON-SPECIFIC IMMUNE DEFENSES BY ADMINISTRATION OF UNDERIVATIZED, AQUEOUS SOLUBLE GLUCANS

[75] Inventors: Spiros Jamas, Boston; D. Davidson Easson, Jr., Shrewsbury; Gary R. Ostroff, Worcester, all of Mass.

[73] Assignee: Alpha-Beta Technology, Inc., Worcester, Mass.

[21] Appl. No.: 400,488

[22] Filed: Mar. 8, 1995

Related U.S. Application Data

[60] Continuation of Ser. No. 257,062, Jun. 9, 1994, abandoned, which is a division of Ser. No. 970,547, Nov. 2, 1992, Pat. No. 5,322,841, which is a continuation of Ser. No. 404,738, Sep. 8, 1989, abandoned.

[51] Int. Cl.$^6$ ................................................. A61K 31/715
[52] U.S. Cl. ........................... 514/54; 514/885; 536/114; 536/121; 536/123; 536/124; 536/123.12; 435/101; 435/255.2
[58] Field of Search ...................... 514/54, 885; 536/114, 536/121, 123, 124, 123.12; 435/101, 255.2

[56] References Cited

U.S. PATENT DOCUMENTS

| | | | |
|---|---|---|---|
| 3,943,247 | 3/1976 | Komatsu et al. | 424/180 |
| 4,138,479 | 2/1979 | Truscheit et al. | 424/88 |
| 4,237,266 | 12/1980 | Sugiura et al. | 536/1 |
| 4,707,471 | 11/1987 | Larm et al. | 514/54 |
| 4,739,046 | 4/1988 | DiLuzio et al. | 536/117 |
| 4,761,402 | 8/1988 | Williams et al. | 514/54 |
| 4,810,646 | 3/1989 | Jamas et al. | 435/101 |
| 4,946,450 | 8/1990 | Erwin | 604/294 |
| 4,975,421 | 12/1990 | Williams et al. | 514/54 |
| 5,032,401 | 7/1991 | Jamas et al. | 424/426 |
| 5,057,503 | 10/1991 | Czop et al. | 514/54 |
| 5,320,849 | 6/1994 | Hagiwara et al. | 424/442 |
| 5,322,841 | 6/1994 | Jamas et al. | 514/54 |
| 5,401,647 | 3/1995 | Tanaka et al. | 435/176 |
| 5,448,040 | 9/1995 | Jamas et al. | 514/54 |
| 5,474,984 | 12/1995 | Tanaka et al. | 514/23 |
| 5,504,079 | 4/1996 | Jamas et al. | 514/54 |

FOREIGN PATENT DOCUMENTS

| | | |
|---|---|---|
| 0463540A1 | 6/1991 | European Pat. Off. . |
| 55-071701 | 8/1980 | Japan . |
| 56076401 | 9/1981 | Japan . |
| 59-045301 | 6/1984 | Japan . |
| 59-210901 | 4/1985 | Japan . |
| 2076418 | 5/1980 | United Kingdom . |
| 91/03248 | 3/1991 | WIPO . |
| 91/03495 | 3/1991 | WIPO . |
| 92/13896 | 8/1992 | WIPO . |
| 94/03498 | 2/1994 | WIPO . |
| 94/03500 | 2/1994 | WIPO . |

OTHER PUBLICATIONS

Vestnik Federalniho Uradu Pro Vynalezy, 10:111 (1989).
Vestnik Federalniho Uradu Pro Vynalezy, 11:122–123 (1989).
Chihara, G., et al., "Lentinan as a Host Defense Potentiator (HPD)," *Int. J. Immunotherapy,* V(4):15–154 (1989).
Sherwood, E.R., et al., "Enhancement of Interleukin–1 and Interleukin–2 Production by Soluble Glucan," *Int. J. Immunopharmac.,* 9(3):261–267 (1987).
Williams, D.L., et al., "Pre–clinical Safety Evaluation of Soluble Glucan," *Int. J. Immunopharmac.,* 10(4):405–414 (1988).
Sasaki et al., "Antitumor Activity of Degraded Products of Lentinan: Its Correlation with Molecular Weight," *Gann(Japanese J. Cancer Res.),* 67(2), 191–195 (Apr. 1976).
DiLuzio et al., "Comparative tumor–Inhibitory and Antibacterial Activity of Soluble and Particulate Glucan (Immuno therapeutic Activity of Soluble Glucan)," *Int. J. Cancer,* 24, 773–779 (1979).
Burgaleta et al., "Effect of Glucan on Granulopoiesis and Macrophage Genesis in Mice," *Cancer Research,* 37, 1739–1742 (Jun. 1977).
Kenyon, "delayed Wound Healing in Mice Associated with Viral Alteration of Macrophages," *Am. J. Vet. Res.,* 44(4), 652–656 (Apr. 1983).
Hobart et al., *A Course on the Molecular and Cellular Basis of Immunity,* Blackwell Scientific Publications, Oxford, UK, (Revised Reprint, 1976), only pp. 317–332 supplied.
Vila et al., "Absence of Viral Rebound After Treatment of HIV–Infected Patients with Didanosine [ddI] and Hydroxycarbamide [Hydroxyurea]," *Lancet,* 350(9078), 635–636 (Aug. 30, 1997).
Janusz, M.J. et al., "Isolation of Soluble Yeast β–Glucans that Inhibit Human Monocyte Phagocytosis Mediated By β–Glucan Receptors", *J. Immunol.* 137:3270–3276 (1986).
Manners, D.J. et al., "the Structure of a β–(1–3)–D–Glucan From Yeast Cell Walls", *Biochem. J.* 135:19–30 (1973).
Williams, D.L. et al., "Pre–Clinical Safety Evaluation of Soluble Glucan", *Chemical Abstracts* 109:66566q (1988).
Fleet, G.H. et al., "Isolation and Composition of an alkali–soluble Glucan from the Cell Walls of *Saccharomyces cerevisiae*", *Chemical Abstracts* 85:89819z (1976).
Bacon, J. et al., "The Glucan Components of the Cell Wall of Baker's Yeast (*Saccharomyces cerevisiae*) Considered in Relation to its Ultrastructure", *Biochem. J.* 114:557–567 (1969).

(List continued on next page.)

*Primary Examiner*—John Kiaht
*Assistant Examiner*—L. Eric Crane
*Attorney, Agent, or Firm*—Hamilton, Brook, Smith and Reynolds, P.C.

[57] ABSTRACT

A method for producing soluble preparations of neutral glucan polymers is disclosed. The method involves treating whole glucan particles with a unique sequence of acid and alkaline treatments to produce soluble glucan. The soluble glucan can be purified to obtain a physiologically acceptable solution of neutral glucan molecules. A soluble neutral glucan preparation is obtained which forms a clear solution at a neutral pH and is equilibrated in a pharmaceutically acceptable carrier.

10 Claims, 2 Drawing Sheets

OTHER PUBLICATIONS

Fleet, G. H. et al., "Isolation and Composition of an Alkali–Soluble Glucan from the Cell Walls of *Saccharomyces cerevisiae*", *Journal of General Microbiology* 94:180–192 (1976.

Latgé, J.P., et al., "Composition Chimique et Ultrastructure des Parois des Corps Hyphaux et des Azygospores de *Conidiobolus obscurus*", *Can. J. Microbiol.* 30:1507–1521 (1984).

Hara, C., et al., "A Branched (1–3)–β–D–Glucan from a Water Extract of *Dictyophora indusiata* FISCH", *Carbohydrate Research* 145:237–246 (1986).

Goldman, R., "Induction of a β–1,3–D–Glucan Receptor in P388D1 Cells Treated with Retinoic Acit or 1,25–dihydroxyvitamin $D_3$", *Immunology* 63:319–324 (1988).

Sherwood et al., "Soluble Glucan and Lymphokine–Activated Killer (LAK) Cells in the Therapy of Experimental Hepatic Metastases", *Chemical Abstracts* 108:179752V (1988).

Konopski, Z. et al., "Phagocytosis of β–1,3–D–Glucan–Derivatized Microbeads by Mouse Peritoneal Macrophages Involves Three Different Receptors", *Scand. J. Immuno.* 33:297–306 (1991).

Reinskind, J.B. et al., "Molecular Architecture of the Hyphal Wall of *Achiya ambisexualis* Raper. II Ultrastructural Analyses and a Proposed Model", *Can J. Microbiol.* 27:1100–1105 (1981).

Miyazaki et al., "Structural Examination of Antiturmour, Water–Soluble Glucans from *Grifora umbellata* by Use of Four types of Glucanase", *Carbohydrate Research* 65:232–243 (1978).

Shiota et al., "Comparison of β–Glucan Structures in a Cell Wall Mutant of *Saccharomyces cerevisiae* and the wild type", *J.Biochem.* 98:1301–1307 (1985).

ENHANCEMENT OF NON-SPECIFIC IMMUNE DEFENSES BY ADMINISTRATION OF UNDERIVATIZED, AQUEOUS SOLUBLE GLUCANS

This application is a continuation of application Ser. No. 08/257,062 filed Jun. 9, 1994 abn, which is a Divisional of U.S. Ser. No. 07/970,547, filed Nov. 2, 1992 U.S. Pat. No. 5,322,841, which is a FWC of U.S. Ser. No. 07/404,738, filed Sep. 8, 1989 (abandoned).

BACKGROUND

Glucans are generally described as polymers of glucose and are derived from yeast, bacteria, fungi and plants. Glucans containing a β(1-3)-linked glucopyranose backbone have long been known to have biological activity, specifically they have been shown to activate the immune system.

Neutral β(1-3) glucan polymers are limited in their utility in parenteral pharmaceutical applications, however, because they are not readily soluble in physiological media. DiLuzio, U.S. Pat. No. 4,739,046 and Williams et al., U.S. Pat. No. 4,761,402. The primary reason for the inherent insolubility of β(1-3) glucans is their tendency to form tightly associated triple-helical fibrils which resist hydration. For this reason, attempts to develop soluble β(1-3) glucans depend on chemical substitution with charged groups, such as phosphate (U.S. Pat. Nos. 4,739,046; 4,761,402), amine (U.S. Pat. No. 4,707,471) or other functional groups (e.g., sulphate) which change the native conformation of the glucan molecules and may affect their biological and pharmacokinetic properties.

SUMMARY OF THE INVENTION

The present invention relates to a method for producing soluble glucan (also referred to as PGG) preparations. In the present method, insoluble glucans are processed through a unique sequence of acid and alkaline treatments to produce soluble glucan. The soluble glucan is then purified at an alkaline pH and below a critical concentration, to obtain a soluble glucan preparation appropriate for parenteral (e.g., intravenous, intraperitoneal, subcutaneous, intramuscular), topic, oral or intranasal administration to humans and animals. Soluble glucan produced by the present method can be maintained in a clear solution when neutralized to pH 7 and equilibrated in a pharmaceutically acceptable carrier. Glucan produced by the present method is a safe, potent immune system enhancer when administered to an individual. Safe and efficacious preparations of soluble glucan polymers of the present invention can be used in therapeutic and/or prophylactic treatment regimens of humans and animals to enhance their immune response.

DETAILED DESCRIPTION OF INVENTION

Figure 1:
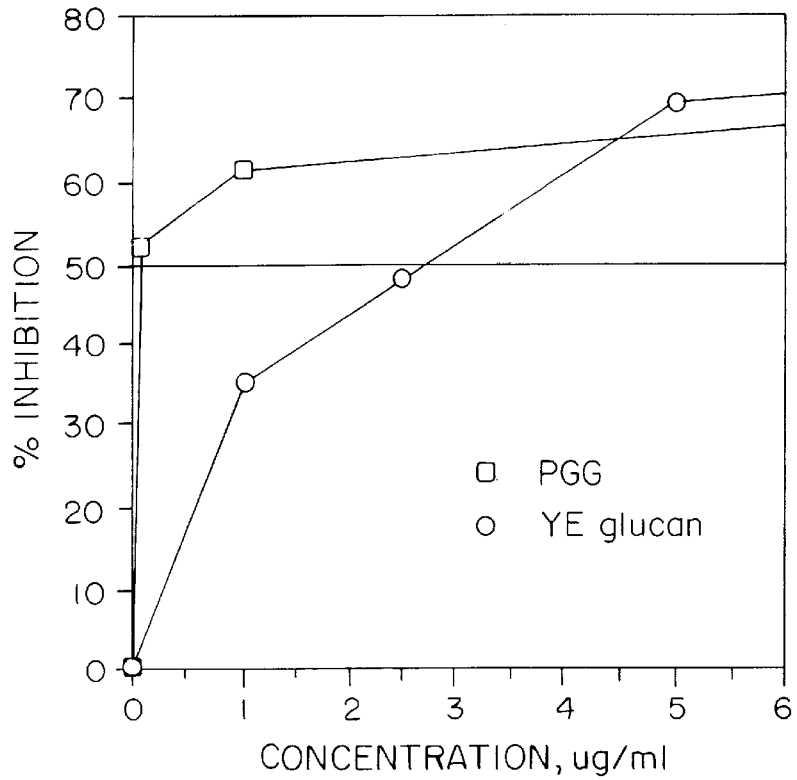
FIG. 1 is a graph showing the dose-dependent inhibitory effect on monocyte ingestion of Zymosan by soluble, modified glucan derived from *S. cerevisiae* R4 compared to yeast extract (YE) glucan.

The soluble glucan preparations of this invention are prepared from insoluble glucan particles. Soluble glucan is also referred to herein as PGG (poly-(1-6)-β-D-glucopyranosyl-(1-3)-β-D-glucopyranose). Preferably, insoluble glucans derived from yeast organisms are employed. Manners et al., *Biol. J.*, 135:19–30, (1973). Glucan particles which are particularly useful as starting materials in the present invention are whole glucan particles described by Jamas et al., in U.S. Pat. Nos. 4,810,646, 4,992,540, 5,082,936 and 5,028,703, the teaching of all are hereby incorporated herein by reference. The source of the whole glucan particles can be the broad spectrum of glucan-containing fungal organisms which contain β-glucans in their cell walls. Whole glucan particles obtained from the strain *Saccharomyces cerevisiae* R4 (NRRL Y-15903) described by Jamas et al. in U.S. Pat. No. 5,028,703 are particularly useful. The structurally modified glucans hereinafter referred to as "modified glucans" derived from *S. cerevisiae* R4 are potent immune system activators, as described in Jamas et al. in co-pending U.S. application Ser. No. 07/404,765 filed concurrently herewith, the teachings of which are hereby incorporated herein by reference.

The whole glucan particles utilized in this present invention can be in the form of a dried powder, as described by Jamas et al., in U.S. Pat. No. 4,810,646 and in co-pending application U.S. Pat. Nos. 4,810,64, 4,922,540, 5,082,936 and 5,028,703. For the purpose of this present invention it is not necessary to conduct the final organic extraction and wash steps described by Jamas et al.

In the present process, whole glucan particles are suspended in an acid solution under conditions sufficient to dissolve the acid-soluble glucan portion. For most glucans, an acid solution having a pH of from about 1 to about 5 and a temperature of from about 20 to about 100° C. is sufficient. Preferably, the acid used is an organic acid capable of dissolving the acid-soluble glucan portion. Acetic acid, at concentrations of from about 0.1 to about 5M or formic acid at concentrations of from about 50% to 98% (w/v) are useful for this purpose. The treatment is preferably carried out at about 90° C. The treatment time may vary from about 1 hour to about 20 hours depending on the acid concentration, temperature and source of whole glucan particles. For example, modified glucans having more β(1-6) branching than naturally-occurring, or wild-type glucans, require more stringent conditions, i.e., longer exposure times and higher temperatures. This acid-treatment step can be repeated under similar or variable conditions. In one embodiment of the present method, modified whole glucan particles from the strain, *S. cerevisiae* R4, which have a higher level of β(1-6) branching than naturally-occuring glucans, are used, and treatment is carried out twice: first with 0.5M acetic acid at 90° C. for 3 hours and second with 0.5M acetic acid at 90° C. for 20 hours.

The acid-insoluble glucan particles are then separated from the solution by an appropriate separation technique, for example, by centrifugation or filtration. The pH of the resulting slurry is adjusted with an alkaline compound such as sodium hydroxide, to a pH of about 7 to about 14. The slurry is then resuspended in hot alkali having a concentration and temperature sufficient to solubilize the glucan polymers. Alkaline compounds which can be used in this step include alkali-metal or alkali-earth metal hydroxides, such as sodium hydroxide or potassium hydroxide, having a concentration of from about 0.1 to about 10N. This step can be conducted at a temperature of from about 4° C. to about 121° C., preferably from about 20° C. to about 100° C. In one embodiment of the process, the conditions utilized are a 1N solution of sodium hydroxide at a temperature of about 80°–100° C. and a contact time of approximately 1–2 hours. The resulting mixture contains solubilized glucan molecules and particulate glucan residue and generally has a dark brown color due to oxidation of contaminating proteins and sugars. The particulate residue is removed from the mixture by an appropriate separation technique, e.g., centrifugation and/or filtration.

The resulting solution contains soluble glucan molecules. This solution can, optionally, be concentrated to effect a 5 to 10 fold concentration of the retentate soluble glucan fraction to obtain a soluble glucan concentration in the range of about 1 to 5 mg/ml. This step can be carried out by an appropriate concentration technique, for example, by ultrafiltration, utilizing membranes with nominal molecular weight levels (NMWL) or cut-offs in the range of about 1,000 to 100,000 daltons. A membrane cut-off of about 10,000 daltons is particularly useful for this step.

The concentrated fraction obtained after this step is enriched in the soluble, biologically active glucan PGG. To obtain a pharmacologically acceptable solution, the glucan concentrate is further purified, for example, by diafiltration. In one embodiment of the present method, diafiltration is carried out using approximately 10 volumes of alkali in the range of about 0.2 to 0.4N. The preferred concentration of the soluble glucan after this step is from about 2 to about 5 mg/ml. The pH of the solution is adjusted in the range of about 7–9 with an acid, such as hydrochloric acid. Traces of proteinaceous material which may be present can be removed by contacting the resulting solution with a positively charged medium such as DEAE-cellulose, QAE-cellulose or Q-Sepharose. Proteinaceous material is detrimental to the quality of the glucan product, may produce a discoloration of the solution and aids in the formation of gel networks, thus limiting the solubility of the neutral glucan polymers. A clear solution is obtained after this step.

The highly purified, clear glucan solution can be further purified, for example, by diafiltration, using a pharmaceutically acceptable medium (e.g., sterile water for injection, phosphate-buffered saline (PBS), isotonic saline, dextrose) suitable for parenteral administration. The preferred membrane for this diafiltraton step has a nominal molecular weight cut-off of about 10,000 daltons. The final concentration of the glucan solution is adjusted in the range of about 0.5 to 5 mg/ml. In accordance with pharmaceutical manufacturing standards for parenteral products, the solution can be terminally sterilized by filtration through a 0.22 μm filter. The soluble glucan preparation obtained by this process is sterile, non-antigenic, and essentially pyrogen-free, and can be stored at room temperature for extended periods of time without degradation.

For purposes of the present invention, the term "soluble" as used herein to describe glucans obtained by the present process, means a visually clear solution can be formed in an aqueous medium such as water, PBS, isotonic saline, or a dextrose solution having a neutral pH (e.g., about pH 5 to about 7.5), at room temperature (about 20°–25° C.) and at a concentration of up to about 10 mg/ml. The term "aqueous medium" refers to water and water-rich phases, particularly to pharmaceutically acceptable aqueous liquids, including PBS, saline and dextrose solutions.

A critical advantage of this method is that precipitation, drying or reconstitution of the soluble glucan polymer is not required at any point in the process. The resulting solution is substantially free of protein contamination, is non-antigenic, non-pyrogenic and is pharmaceutically acceptable for parenteral administration to animals and humans. However, if desired, the soluble glucan can be dried by an appropriate drying method, such as lyophilization, and stored in dry form. The dried glucan can be reconstituted prior to use by adding an alkali solution such as about 0.1–0.4N NaOH and reprocessed starting from the step immediately following the organic acid contact steps described above.

The soluble glucans produced by the method of this invention are branched polymers of glucose, referred to as PGG, containing $\beta(1-3)$ and $\beta(1-6)$ linkages in varying ratios depending on the organism and processing conditions employed. The PGG glucan preparations contain neutral glucans, which have not been modified by substitution with functional (e.g., charged) groups or other covalent attachments. The biological activity of PGG glucan can be controlled by varying the average molecular weight and the ratio of $\beta(1-6)$ to $\beta(1-3)$ linkages of the glucan molecules, as described by Jamas et al. in U.S. Pat. Nos. 4,810,646, 4,992,540, 5,082,936 and 5,028,703. The average molecular weight of soluble glucans produced by the present method is generally from about 10,000 to about 500,000 daltons, preferably from about 30,000 to about 50,000.

The present soluble glucan preparations can be used as safe, effective, therapeutic and/or prophylactic agents, either alone or as adjuvants, to enhance the immune response in humans and animals. Soluble glucans produced by the present method enhance or prime the immune system so that the immune response is quicker and more pronounced. The present soluble glucan composition can be used to prevent or treat infectious diseases in malnourished patients, patients undergoing surgery, patients undergoing chemotherapy or radiotherapy, HIV-infected patients and the elderly, all of whom may have weakened immune systems. Methods of treating immunocompromised patients with glucans are described in detail in co-pending U.S. application Ser. No. 07/409,765 by Jamas et al. filed concurrently herewith.

The present composition is generally administered to an animal or a human in an amount sufficient to produce immune system enhancement. The preparation can be administered parenterally by injection, e.g., intravenously, intramuscularly, intraperitoneally, subcutaneously, topically, orally or intranasaly. The soluble glucans can be administered as a clear solution having a concentration of from about 1 mg/ml to about 5 mg/ml. The solvent can be a physiologically acceptable aqueous medium, such as water, saline, PBS or a 5% dextrose solution. The amount necessary to induce immune system enhancement will vary on an individual basis and be based at least in part on consideration of the individual's size, the severity of the symptoms and the results sought.

PGG is a non-toxic, non-antigenic glucan preparation which enhances or primes the body's natural defense against infection, particularly for patients with normal or decreased immunologic function, so that the normal immune response is faster and more pronounced. Parenteral administration of PGG mimics the natural physiologic response to an infectious challenge by enhancing the balanced, endogenous release of cytokines in appropriate quantities and proportions. PGG can be used for the prevention and treatment of infections caused by a broad spectrum of bacterial, fungal, viral and protozoan pathogens. The prophylactic administration of PGG to a person undergoing surgery, either preoperatively, intraoperatively and/or post-operatively, will reduce the incidence and severity of post-operative infections in both normal and high-risk patients. For example, in patients undergoing surgical procedures that are classified as contaminated or potentially contaminated (e.g., gastrointestinal surgery, hysterectomy, cesarean section, transurethal prostatectomy) and in patients in whom infection at the operative site would present a serious risk (e.g., prosthetic arthroplasty, cardiovascular surgery), concurrent initial therapy with an appropriate antibacterial agent and the present PGG preparation will reduce the incidence and severity of infectious complications.

In patients who are immunosuppressed, not only by disease (e.g., cancer, AIDS) but by courses of chemotherapy and/or radiotherapy, the prophylactic administration of PGG will reduce the incidence of infections caused by a broad spectrum of opportunistic pathogens including many unusual bacteria, fungi and viruses. Therapy using PGG has demonstrated a significant radioprotective effect with its ability to enhance and prolong macrophage function and regeneration and, as a result enhance resistance to microbial invasion and infection.

In high risk patients (e.g., over age 65, diabetics, patients having cancer, malnutrition, renal disease, emphysema, dehydration, restricted mobility, etc.) hospitalization frequently is associated with a high incidence of serious nosocomial infection. Treatment with PGG glucan may be started empirically before catheterization, use of respirators, drainage tubes, intensive care units, prolonged hospitalizations, etc. to help prevent the infections that are commonly associated with these procedures. Concurrent therapy with antimicrobial agents and the PGG is indicated for the treatment of chronic, severe, refractory, complex and difficult to treat infections.

Glucan produced by the present method enhances the non-specific defenses of mammalian mononuclear cells and significantly increases their ability to respond to an infectious challenge. The unique property of glucan-macrophage activation is that it does not result in increased body temperatures (i.e., fever) as has been reported with many non-specific stimulants of host defenses. This critical advantage of glucan may lie in the natural profile of responses it mediates in white blood cells. A unique mechanism of glucan activity in vitro is that pre-treatment of normal human leukocytes with PGG appears to prime the mononuclear cells to release elevated levels of monokines (TNF, GM-CSF, M-CSF, IL-6) upon subsequent stimulation with endotoxin or other infectious agents. This is considered highly advantageous since the monokines are not released systemically until exposure to the infectious agent. Thus, the present invention provides a soluble glucan which can be parenterally, topically, intranasaly, or orally administered to an animal or human to enhance the immune system, and a method for producing the soluble glucan.

The invention is further illustrated by the following Examples.

EXAMPLES

Example 1
Preparation of PGG from Dried Whole Glucan Particles

Whole glucan particles were prepared from dried Baker's Yeast (Universal Foods, Wis.) according to the procedure of Jamas et al., U.S. Pat. No. 4,810,646. 100 grams of the resulting dried whole glucan particles were resuspended in 3 liters of 90% formic acid and stirred at room temperature for 1 hour. The mixture was then heated to 80° C. and stirred until a sudden drop in viscosity was observed. At this point, 9 liters of ethanol were added to the mixture resulting in formation of a precipitate, which was collected by centrifugation. The precipitate was then dissolved in 0.4M sodium hydroxide (NaOH) and the solution was centrifuged to remove undissolved particulates. The supernatant was concentrated by ultrafiltration using an Immersible-Cx-30 Ultrafilter (Millipore Corp., Bedford, Mass.) with a 30,000 dalton nominal molecular weight limit (NMWL) cut off. The retentate fraction was then diafiltered with ten volumes of water using the same equipment. The resulting solution was concentrated and equilibrated in sterile isotonic saline by diafiltration. The final yield of this fraction (>30,000 daltons) was 1.9 grams.

To produce a 10,000–30,000 fraction, the filtrate from the first ultrafiltration was concentrated by ultrafiltration through a 10,000 dalton membrane using an Immersible-CX-10 Ultrafilter (Millipore Corp.). The concentrated retentate fraction was then diafiltered with ten volumes of water, followed by equilibration in sterile isotonic saline. The final yield of this fraction was 2.7 grams.

Example 2
Production of PGG from Saccharomyces cerevisiae R4

Saccharomyces cerevisiae R4 (NRRL Y-15903) was cultured in 60 liters of a defined growth medium (4.45 g/l $KH_2PO_4$, 3.0 g/L $(NH_4)_2SO_4$, 1.1 g/l $MgSO_4 \cdot 7H_2O$, 1.8 g/l Lysine-HCl, 0.9 g/l Tyrosine, 0.012 g/l Adenine, 0.012 g/l Uracil, 5.0 g/l casamino acids, 0.45 g/l Histidine and 4.0 g/l Glucose) in a MPP-80 Mobile Pilot Plant Fermenter (New Brunswick Scientific, New Jersey). When the culture reached an optical density (OD, 600 nm) of 30 the fermentation was stopped by adjusting the pH to 12 with 5M sodium hydroxide. The total cell yield was approximately 1.8 kg dry cell weight. The cells were harvested by centrifugation using a Westfalia Nozzle Bowl Separator (Model SKOG-205, Centrico, N.J.) and were washed with water. The concentrated cell suspension was transferred to a stainless steel stirred vessel and resuspended in 10 liters of 1M sodium hydroxide and stirred for 20 hours at 25° C. The mixture was then heated to 90° C. and stirred for an additional 1 hour. The insoluble particles were collected by centrifugation and washed with water. The concentrated slurry was resuspended to a volume of 10 liters in 1M sodium hydroxide and stirred at 90° C. for 3 hours. This extraction step was repeated at 90° C. for 1 hour. The insolubles were collected by centrifugation and washed with water. The concentrated slurry was then resuspended in 10 liters of water, the pH was adjusted to 4.5 with hydrochloric acid and stirred at 90° C. for 1 hour, followed by centrifugation and washing. The concentrated slurry was then resuspended in 5 liters of 0.5M acetic acid and stirred at 90° C. for 3 hours. The insolubles were collected by centrifugation. The yield of glucan particles at this step was 2.8 kg net weight.

An aliquot of 100 grams of the insoluble glucan particles was then resuspended in 500 ml of 0.5M acetic acid and was extracted at 90° C. for 20 hours. The suspension was then neutralized to pH 7 with sodium hydroxide, and the insoluble glucan particles were collected by centrifugation. The glucans were resuspended in 200 ml of 1M sodium hydroxide and heated to 90° C. for 1 hour to solubilize the glucan. The mixture was cooled and centrifuged to remove particulate debris. The supernatent solution was diluted to 0.4M sodium hydroxide with water and was filtered through a 0.5 μm polypropylene depth filter. The resulting solution was concentrated four-fold by ultrafiltration through a 10,000 dalton NMWL membrane using a Minitan HRTF System (Millipore Corp.).

The retentate fraction was then diafiltered with ten volumes of 0.4M sodium hydroxide using the same equipment.

The solution was diluted to obtain a 2 mg/ml glucan solution in 0.225M sodium hydroxide. The solution was adjusted to pH 9 with hydrochloric acid and diafiltered against sterile, isotonic saline using the Minitan System. The solution was then filtered through a 0.22 μm sterilizing filter. This procedure gave 1.1 grams of sterile PGG glucan with a weight average molecular weight of 225,000 daltons.

Example 3
Affinity of Modified Glucans for the Monotype β-glucan Receptor

The ability of glucan molecules to be recognized and bound to the β-glucan receptor of monocytes is critical for their biological activity. Modified whole glucans derived from the mutant strain R4 (WGP-R4) demonstrated an increased affinity for the glucan receptor of monocytes when compare to naturally occurring glucans from Baker's yeast. Janusz et al., *J. of Immunol.*, 137:3270–3276 (1986).

Water-soluble modified glucan (PGG) was prepared from WGP-R4 according to the procedure outlined in Example 2.

Human monocytes were incubated with various concentrations of the PGG for 15 minutes, washed to remove unbound glucan and then incubated with Zymosan for 30 minutes. After fixing and staining the monolayers, the percentage of monocytes ingesting Zymosan was determined. The affinity of glucan preparations for the β-glucan receptor was measured according to their ability to competitively occupy the receptor thus inhibiting the uptake of Zymosan by monocytes. Samples were compared by taking the concentration of glucan required to obtain 50% inhibition of Zymosan ingestion.

The significantly enhanced affinity of the soluble PGG glucan derived from WGP-R4 to the receptor is evident by the low concentration required to obtain a 50% inhibition of Zymosan ingestion. The results, presented in FIG. 1, demonstrate that the PGG glucan, designated WGP-R4, binds to the monocyte β-glucan receptor with a much higher affinity (0.1 μg/ml) than soluble glucan from Baker's yeast extract (3.5 μg/ml), (YE glucan) representing a 35-fold increase in activity.

Example 4
Effect of PGG Molecular Weight on Macrophage Phagocytosis

Two molecular weight fractions of PGG from *Saccharomyces cerevisiae* R4 were prepared according to the procedure outlined in Example 2. The PGG preparations were then assayed for their affinity for the monocyte β-glucan receptor by measuring inhibition of Zymosan phagocytosis as described in Example 3. The results, shown in Table 1 demonstrate that the molecular weight of the PGG preparations affects their affinity for the β-glucan receptor, and therefore is expected to affect their in vivo immunologic activity.

TABLE 1

Effect of PGG Molecular Weight on Receptor Binding

| Glucan | Concentration for 50% Inhibition μg/ml | Relative Avidity |
|---|---|---|
| Barley β-Glucan[1] | 65 | 1 |
| PGG-R4 Modified Glucan NW - 20,000 d | 0.6 | 108 |
| PGG-R4 Modified Glucan MW - 330,000 | 0.1 | 650 |

[1]Czop and Austen., J. Immunology, 135(5):3388–3393, (1985).

Example 5
In Vivo Activity of PGG Glucans

The effect of in vivo administration of modified glucans on peripheral white blood cell (WBC) counts was characterized in mice. PGG preparations of the modified glucan from strain R4 were prepared according to the procedure outlined in Example 2 and administered intravenously (IV) and subcutaneously (SC) to male CD-1 mice. Total and differential cell counts were monitored at regular time intervals.

Figure 2:
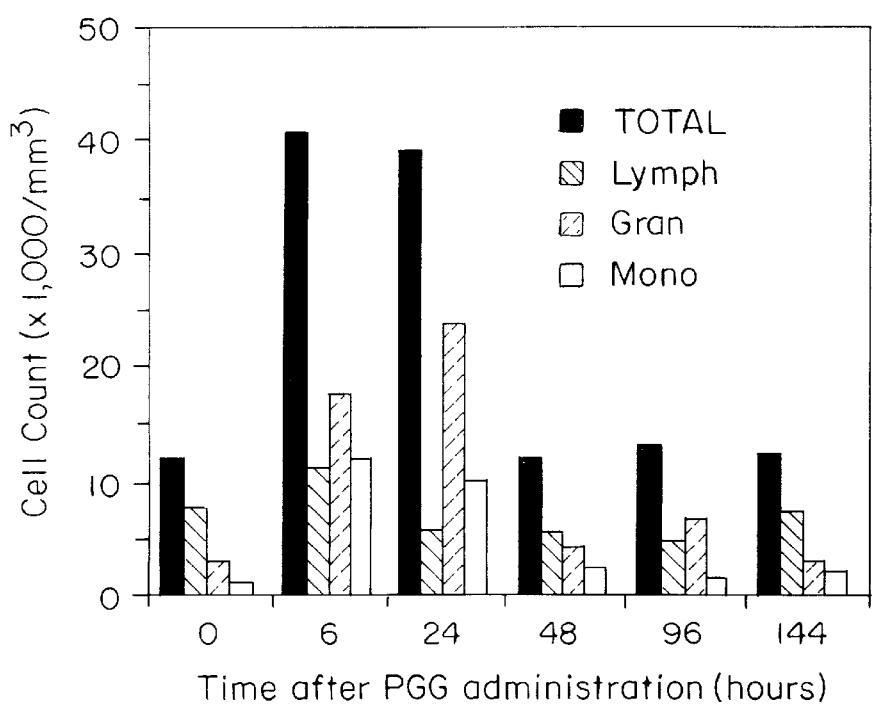
FIG. 2 is a graph showing the change in peripheral total and differential white blood cell (WBC) counts in mice after a single, intravenous dose of PGG (5 mg/mouse).
Figure 3:
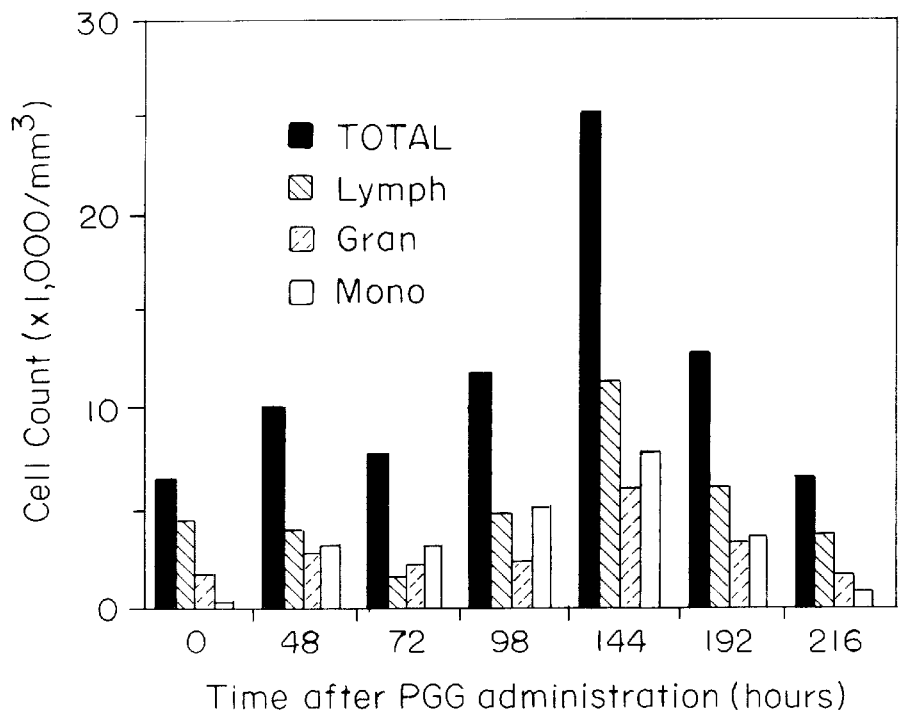
FIG. 3 is a graph showing peripheral total and differential white blood cell (WBC) counts in mice after multiple dose subcutaneous administration of PGG (5 mg/mouse/day×4 days).

A profound increase in the total WBC count was observed particularly following single-dose IV administration of PGG. FIGS. 2 and 3 summarize the results, which show rapid (<6 hours) amplification of total WBC counts with, the most pronounced increase (12× and 6×) occurring in the monocyte and granulocyte counts, respectively. This is consistent with in vitro data suggesting the presence of a high affinity β-glucan receptor present on human monocytes. The multiple-dose SC regimen (FIG. 3) elicited an increase in total WBC beginning at 48 hours and peaking at 144 hours after initiation of therapy. The increase in total counts was consistent with an increase in the peripheral monocyte population over this time period. The average monocyte count increased from 320/mm$^3$ at zero hours to approximately 8,000/mm$^3$ at 144 hours, representing at 24-fold increase.

Example 6
Infection Model

A sepsis model was developed in mice to characterize the efficacy of modified PGG glucans in protecting an immunologically intact host against serious infections, such as those which commonly occur following abdominal surgery. PGG derived from WGP-R4 was prepared according to the procedure outlined in Example 2.

Figure 4:
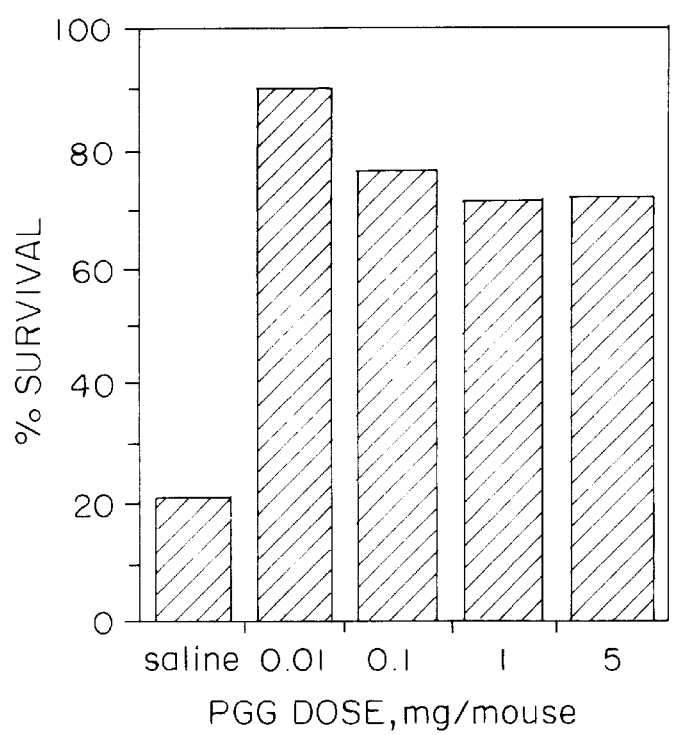
FIG. 4 is a graph showing the efficacy of the PGG glucans in an *E. coli* sepsis model in mice.

The model used intraperitoneal challenge of mice with an 0.1 ml suspension of *E. coli* strain TVDL-rat (approximately 10 CFU/ml) 24 hours following IV administration of PGG by single bolus injection using transthoracic cardiac puncture. Mice were returned to their cages and maintained on food, and water ad libitum. A control group of 10 mice were injected with 0.1 ml sterile saline at the time of the PGG administration. Mortality rates for the treatment groups and saline control group were recorded at 48 hours after challenge. The results, shown in FIG. 4, demonstrated that PGG obtained from the modified glucan, WGP-R4, significantly reduced mortality, as compared to the saline control group (p<0.05) at doses as low as 0.01 mg/mouse (0.5 mg/kg body weight).

Equivalents

Those skilled in the art will recognize, or be able to ascertain, using no more than routine experimentation, many equivalents to the specific embodiments of the invention described specifically herein. Such equivalents are intended to be encompassed in the scope of the following claims.

We claim:
1. A method of treating an immunocompromised human or animal comprising administering to said human or animal an amount of an underivatized, aqueous soluble yeast β(1-3) glucan sufficient to enhance the non-specific defenses of mononuclear cells or macrophages or both in said animal or human, wherein the underivatized, aqueous soluble yeast β(1-3) glucan is produced by a process comprising the steps of:
   a) contacting a suspension of aqueous insoluble β(1-3) glucan derived from yeast with an organic acid to solubilize said glucan thereby forming an acid-soluble and acid-insoluble glucan mixture;

b) contacting the acid-soluble portion of the glucans with an alkali solution to dissolve the alkali-soluble glucan;

c) removing alkali-insoluble glucans from the solution of step (b);

d) neutralizing the solution containing the alkali-soluble glucan of step (c); and e) isolating an aqueous soluble β(1-3) glucan by size fractionation to produce a β(1-3) glucan that is suitable for parenteral administration, thereby treating said immunocompromised human or animal by enhancing the non-specific defenses of mononuclear cells or macrophages or both.

2. The method of claim 1 wherein the yeast is a strain of *Saccharomyces cerevisiae*.

3. The method of claim 1 wherein the soluble yeast β(1-3) glucan is administered parenterally, topically, orally or intranasally.

4. The method of claim 1 wherein the soluble yeast β(1-3) glucan is contained in a physiologically acceptable medium.

5. The method of claim 4 wherein the physiologically acceptable medium is selected from the group consisting of sterile water, phosphate-buffered saline, isotonic saline and dextrose.

6. The method of claim 1, further comprising purifying the aqueous soluble yeast β(1-3) glucan by size fractionation or diafiltration with a physiologically acceptable medium.

7. A method of claim 2, wherein the strain of *Saccharomyces cerevisiae* is strain R4 (NRRL accession number Y-15903).

8. A method of treating an immunocompromised human or animal comprising administering to said human or animal an amount of an underivatized, aqueous soluble yeast β(1-3) glucan sufficient to enhance the non-specific defenses of mononuclear cells or macrophages or both in said animal or human, thereby treating said immunocompromised human or animal by enhancing the non-specific defenses of mononuclear cells or macrophages or both.

9. The method of claim 8 wherein the yeast is a strain of *Saccharomyces cerevisiae*.

10. A method of claim 9, wherein the strain of *Saccharomyces cerevisiae* is strain R4 (NRRL accession number Y-15903).

* * * * *